US005663184A

United States Patent [19]
Bryant et al.

[11] Patent Number: 5,663,184
[45] Date of Patent: Sep. 2, 1997

[54] METHODS OF INHIBITING CNS PROBLEMS IN POST-MENOPAUSAL WOMEN

[75] Inventors: Henry U. Bryant, Indianapolis; Andrew L. Glasebrook, Zionsville; Timothy A. Grese, Indianapolis; David L. Phillips, Clayton, all of Ind.

[73] Assignee: Eli Lilly and Company, Indianapolis, Ind.

[21] Appl. No.: 432,438

[22] Filed: Apr. 28, 1995

Related U.S. Application Data

[63] Continuation of Ser. No. 171,388, Dec. 21, 1993.

[51] Int. Cl.$^6$ .................. A61K 31/445; A61K 31/40; A61K 31/38
[52] U.S. Cl. .................. 514/324; 514/408; 514/422; 514/443
[58] Field of Search .................. 514/324, 408, 514/422, 443

[56] References Cited

U.S. PATENT DOCUMENTS

| | | |
|---|---|---|
| 4,133,814 | 1/1979 | Jones et al. |
| 4,380,635 | 4/1983 | Peters. |
| 4,418,068 | 11/1983 | Jones. |
| 4,894,373 | 1/1990 | Young .................. 514/239 |
| 5,075,321 | 12/1991 | Schreiber. |
| 5,492,927 | 2/1996 | Gitter et al. |

FOREIGN PATENT DOCUMENTS

| | | |
|---|---|---|
| 0178862 | 4/1986 | European Pat. Off. |
| 4320896 A1 | 6/1993 | Germany. |
| WO93/10113 | 5/1993 | Japan. |
| 1064629 | 4/1967 | United Kingdom. |
| WO93/1074 | 6/1993 | WIPO. |

OTHER PUBLICATIONS

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18-22, 1993.

Bryant et al., "Raloxifene is a Tissue Specific Estrogen Agonist", Am Soc. Bone & Min. Res., Tampa, Sep. 18-22, 1993.

Frolick et al., "In Vivo and In Vitro Metabolism of Raloxifene", Am. Soc. Bone & Min. Res., Tampa, Sep. 18-22, 1993.

Glasebrook et al., "Multiple Binding Sites for the Anti-estrogen Raloxifene", Am. Soc. Bone & Min. Res., Tampa, Sep. 18-22, 1993.

Hock et al., "Combination of Raloxifene and Human Parathyoid Hormone 1-34; Increased Femur Bone Mass in Young Ovariectomized (OVX) Rats", Am. Soc. Bone & Min. Res., Tampa, Sep. 18-22, 1993.

Sato et al., "DEXA Analysis of Raloxifene Effects on the Bones From Ovariectomized Rats", Am. Soc. for Bone and Min. Res., Tampa, Sep. 18-22, 1993.

Yang et al., "Raloxifene an Anti-Estrogen, Simulates the Effects of Estrogen in Inhibiting Bone Resorption Through Regulating TGFB-3 Expression in Bone;".Am Soc. for Bone and Min. Res., Tampa, Sep. 18-22, 1993.

Black et al., "Distinct, Structure-Related Profiles of Estrogenic and Anti-Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice." Life Sciences, 26:1980, 1453-1458.

Black et al., "Differential Interaction of Antiestrogens with Cytosol Estrogen Receptors," Molecular and Cellular Endocrinology, 22:1981, 95-103.

Black et al., "Evidence for Biological Action of the Antiestrogens LY117018 and Tamoxifen by Different Mechanisms," Endocrinology 109:1981, 987-989.

Black, L.J. "Biological Actions and Binding Proprieties of a New Estrogen Antagosist LY117018," In: Homone Antagonists, 129-82, 1982 (M.K. Agarwal ed.) Walter de Gruyter and Co., Berlin New York.

Black et al., LY156758: A Unique Antiestrogen Displaying High Affinity for Estrogen Receptors, Negligible Estrogenic Activity and Near-Total Estrogen Antagonism in Vivo. Presented at the Fifth Annual San Antonio Breast Cancer Symposium, San Antonio, Texas, Nov. 5-6, 1982.

(List continued on next page.)

*Primary Examiner*—Zohreh Fay
*Attorney, Agent, or Firm*—James J. Sales

[57] ABSTRACT

A method of inhibiting one or more CNS disorders in a post-menopausal woman comprising administering to a female human in need of treatment an effective amount of a compound having the formula $$\text{(I)}$$

wherein $R^1$ and $R^3$ are independently hydrogen, —$CH_3$, $$\underset{\overset{\|}{O}}{-C}-(C_1-C_6\text{alkyl}), \text{ or } \underset{\overset{\|}{O}}{-C}-Ar,$$

wherein Ar is optionally substituted phenyl;

$R^2$ is selected from the group consisting of pyrrolidine, hexamethyleneamino, and piperidino; or a pharmaceutically acceptable salt of solvate thereof.

3 Claims, No Drawings

OTHER PUBLICATIONS

Black et al., The Antiestrogenic Action of LY139481: Species Uniformity Duration of Action and Kinetics of 3H-LY139481 Distribution In Vivo. Sixty-fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Chemistry 22; 1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl] [4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

METHODS OF INHIBITING CNS PROBLEMS IN POST-MENOPAUSAL WOMEN

This application is a continuation of application Ser. No. 08/171,388 filed Dec. 21, 1993.

BACKGROUND OF THE INVENTION

In climacteric women, anxiety, depression tension and irritability begin during the perimenopause and can be correlated to reduced estrogen levels and estrogen replacement therapy has been recommended for the treatment of these symptoms (Malleson J., *Lancet*, 2: 158, (1953); Wilson et. al., *J. Am. Geriatric Soc.*, 11: 347 (1963)). The mechanism for protective effects of estrogen in this case is unknown, but may be related to potential effects of estrogen on biogenic amines such as serotonin (Aylward M., *Int. Res. Communications System Med. Sci.*, 1: 30 (1973)). To this regard circulating serotonin is reduced in post-menopausal women (Gonzales G., et. al., *Maturitas* 17: 23–29 (1993)), and serotonin (as well as several other biogenic amines) have a putative role in behavioral depression.

Phillips and Sherwin (*Psychoneuroendocrinology*, 17: 485–495 (1992)) reported that in surgically menopausal women given estrogen, scores in immediate and delayed recall tests are greater than in similar women not given estrogen. Two potential hypotheses might explain this effect. There is some evidence that partial estrogen agonists (or anti-estrogens) such as tamoxifen interact with the muscarinic receptor (Ben-Baruch G., et. al., *Molec. Pharmacol.* 21: 287–293 1982), and muscarinic agonists ($M_2$) are known to produce positive effects in a number of memory associated tasks and may have clinical relevance in Alzheimer's Disease. Another interesting possibility may be linked to neurokinins such as Substance P, which are known to have neurotrophic as well as memory-promoting effects (Thoenen H., *Trends in Neuroscience*, 14: 165–170 (1991); Huston J. et. al., *Neurosci. Biobehav. Rev.* 13: 171–180 (1989)), thus, through an effect either at a neurotransmitter receptor in the CNS or at a neuropeptide receptor, a tissue selective estrogen agonist/antagonist could produce memory and cognitive enhancing effects. Such an activity would most relevantly be assessed in man, but a variety of animal models (i.e. maze learning, extinction etc.) are available for preclinical testing.

Perhaps the most frequent CNS related problem in climacteric women is the occurrence of hot flushes. While this undoubtedly is a somatic effect mediated by effects on the microvasculature, current evidence points strongly in the direction of CNS initiated effect (Lomax P., et. al., *Pharmac. Ther.* 57: 347–358 (1993)). Therefore, a tissue selective estrogen agonist/antagonist like raloxifene might offer the ideal therapy providing the desired effect in the absence of untoward side effects on reproductive tissue.

SUMMARY OF THE INVENTION

This invention provides methods for inhibiting CNS problems in a post-menopausal female comprising administering to a female human in need of treatment an effective amount of a compound of formula I

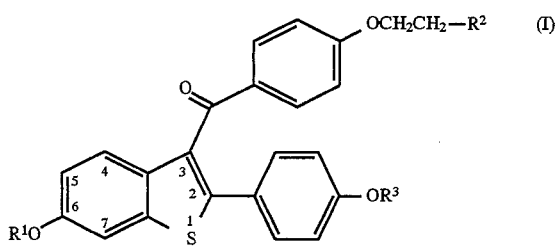

wherein $R^1$ and $R^3$ are independently hydrogen, —$CH_3$,

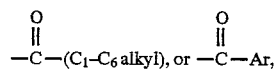

wherein Ar is optionally substituted phenyl;
$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting CNS disorders in a post-menopausal woman. The methods of treatment provided by this invention are practiced by administering to a human in need of a dose of a compound of formula I or a pharmaceutically acceptable salt or solvate thereof, that is effective to inhibit one or more CNS disorders. The term inhibit is defined to include its generally accepted meaning which includes prophylactically treating a human subject to incurring the characteristics described, and holding in check and/or treating existing characteristics. As such, the present method includes both medical therapeutic and/or prophylactic treatment, as appropriate. CNS disorders are those disorders known to be included in the definition by those skilled in the art, which affect post-menopausal women, which includes anxiety, depression, mood swings, tension, irritability, motivational defects, memory loss and cognitive disorders.

Raloxifene, a compound of this invention wherein it is the hydrochloride salt of a compound of formula 1, $R^1$ and $R^3$ are hydrogen and $R^2$ is 1-piperidinyl, is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, Raloxifene activates the same genes as estrogen does and displays the same pharmacology, e.g., inhibit bone loss, lower serum lipids. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each. This is not to say, however, that the mechanism of action is necessarily mediated either at all or in part, through the estrogen receptor per se.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418, 068, and 4,380,635 all of which are incorporated by reference herein. In general, the process starts with a benzo[b] thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Substituted phenyl includes phenyl substituted once or twice with $C_1$-$C_6$ alkyl, $C_1$-$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit one or more CNS disorders in a postmenopausal female, according to this invention, will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed to effectively treat the symptoms.

It is usually preferred to administer a compound of formula I in the form of an acid addition salt, as is customary in the administration of pharmaceuticals bearing a basic group, such as the piperidino ring. It is also advantageous to administer such a compound by the oral route to an aging human (e.g. a post-menopausal female). For such purposes the following oral dosage forms are available.

FORMULATIONS

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of the raloxifene that have been made include those shown below:

Formulation 2: Raloxifene Capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene Capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene Capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene Capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

TEST PROCEDURE

Five to fifty women are selected for the clinical study. The women are post-menopausal, i.e., have ceased menstruating for between 6 and 12 months prior to the study's initiation, are in good general health, and suffer from one or more of the above-mentioned CNS disorders. Because of the idiosyncratic and subjective nature of these disorders, the study has a placebo control group, i.e., the women are divided into two groups, one of which receive the active agent of this invention and the other receive a placebo. Women in the test group receive between 50–200 mg of the drug per day by the oral route. They continue this therapy for 3–12 months. Accurate records are kept as to the number and severity of the above mentioned disorders in both groups and at the end of the study these results are compared. The results are compared both between members of each group and also the results for each patient are compared to the disorders reported by each patient before the study began.

Utility of the compounds of the invention is illustrated by the positive impact they have on one or more of the CNS symptoms/disorders when used in a study as above.

We claim:

1. A method of inhibiting one or more CNS disorders in a post-menopausal female selected from the group consisting of anxiety, depression mood swings, tension, irritability, motivational defects, memory loss and cognitive disorders comprising prophylactically administering to a female human in need of treatment an effective amount of a compound having the formula

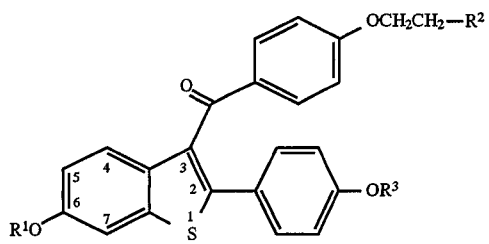

wherein $R^1$ and $R^3$ are independently hydrogen, —$CH_3$,

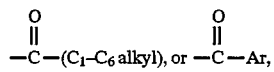

wherein Ar is optionally substituted phenyl;

$R^2$ is selected from the group consisting of pyrrolidine, hexamethyleneimino, and piperidino; or a pharmaceutically acceptable salt of solvate thereof.

2. The method of claim 1 wherein said compound is the hydrochloride salt thereof.

3. The method of claim 1 wherein said compound is

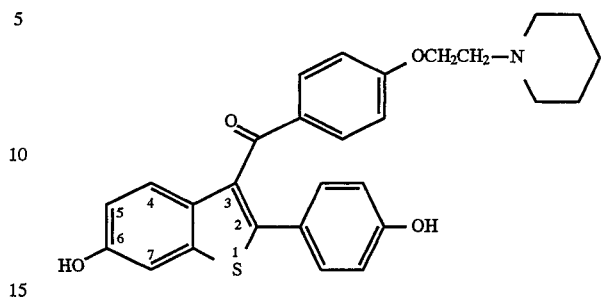

or its hydrochloride salt.

* * * * *